(12) United States Patent
Ainsworth et al.

(10) Patent No.: US 7,783,338 B2
(45) Date of Patent: Aug. 24, 2010

(54) CATHETER WITH OPTICAL FIBER SENSOR

(75) Inventors: Robert Ainsworth, Scotts Valley, CA (US); Deborah Kilpatrick, Los Altos, CA (US); Jeong S. Lee, Diamond Bar, CA (US); Bridget A. Hurley, San Francisco, CA (US); Jeffrey T. Ellis, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 20 days.

(21) Appl. No.: 12/008,381

(22) Filed: Jan. 9, 2008

(65) Prior Publication Data

US 2008/0139897 A1    Jun. 12, 2008

Related U.S. Application Data

(63) Continuation of application No. 09/872,310, filed on May 31, 2001, now Pat. No. 7,329,223.

(51) Int. Cl.
*A61B 5/00* (2006.01)
(52) U.S. Cl. .............. 600/478; 600/300; 600/310; 600/322; 600/339; 600/342; 600/424; 600/431; 600/479; 600/549; 606/1; 606/194; 604/96.01
(58) Field of Classification Search ............ 600/108, 600/160, 180, 204, 300, 310, 322–328, 339, 600/341, 342, 407, 411, 424, 425, 427, 431, 600/433–435, 473, 474, 476, 478, 479, 481–483, 600/504, 505, 549; 604/96.01; 606/1, 2, 606/7, 13–16, 191, 192, 194
See application file for complete search history.

(56) References Cited

U.S. PATENT DOCUMENTS

| 4,587,972 | A | 5/1986 | Morantte, Jr. |
| 4,619,274 | A | 10/1986 | Morrison |
| 4,671,288 | A | 6/1987 | Gough |
| 4,794,931 | A | 1/1989 | Yock |
| 4,841,977 | A | 6/1989 | Griffith et al. |
| 4,887,605 | A | 12/1989 | Angelsen et al. |
| 4,920,967 | A | 5/1990 | Cottonaro et al. |

(Continued)

OTHER PUBLICATIONS

Beekhuizen H, van Furth R. "Monocyte Adherence to Human Vascular Endothelium." *Journal of Leukocyte Biology* 1993, vol. 54, 363-378.

(Continued)

*Primary Examiner*—Ruth S Smith
(74) *Attorney, Agent, or Firm*—Blakely Sokoloff Taylor & Zafman LLP

(57) ABSTRACT

An apparatus and method to perform therapeutic treatment and diagnosis of a patient's vasculature through the use of an intravascular device having an optical fiber disposed therein. In an embodiment, the apparatus includes an intravascular device to perform a therapeutic treatment and at least one optical fiber disposed through the intravascular device. The optical fiber is configured to provide diagnostic information before, during, and after the therapeutic treatment. In an embodiment, diagnostic information includes vessel and blood characteristics such as hemodynamic characteristics, hematological parameters related to blood and blood components, and thermal parameters of the vasculature.

25 Claims, 12 Drawing Sheets

U.S. PATENT DOCUMENTS

| | | | |
|---|---|---|---|
| 4,926,875 | A | 5/1990 | Rabinovitz et al. |
| 4,941,473 | A | 7/1990 | Tenerz et al. |
| 5,022,399 | A | 6/1991 | Biegeleisen |
| 5,047,213 | A | 9/1991 | Finlan et al. |
| 5,167,233 | A | 12/1992 | Eberle et al. |
| 5,199,431 | A | 4/1993 | Kittrell et al. |
| 5,284,146 | A | 2/1994 | Czar et al. |
| 5,325,860 | A | 7/1994 | Seward et al. |
| RE34,695 | E | 8/1994 | Mar et al. |
| 5,345,940 | A | 9/1994 | Seward et al. |
| 5,372,138 | A | 12/1994 | Crowley et al. |
| 5,456,251 | A | 10/1995 | Fiddian-Green |
| 5,487,972 | A | 1/1996 | Gelfand et al. |
| 5,514,128 | A | 5/1996 | Hillsman et al. |
| 5,571,086 | A | 11/1996 | Kaplan et al. |
| 5,582,171 | A | 12/1996 | Chornenky et al. |
| 5,599,492 | A | 2/1997 | Engelson |
| 5,601,087 | A | 2/1997 | Gunderson et al. |
| 5,603,820 | A | 2/1997 | Malinski et al. |
| 5,693,043 | A | 12/1997 | Kittrell et al. |
| 5,744,902 | A | 4/1998 | Vig |
| 5,752,518 | A | 5/1998 | McGee et al. |
| 5,756,351 | A | 5/1998 | Isacoff et al. |
| 5,782,760 | A | 7/1998 | Schaer |
| 5,848,969 | A | 12/1998 | Panescu et al. |
| 5,855,563 | A | 1/1999 | Kaplan et al. |
| 5,873,835 | A | 2/1999 | Hastings et al. |
| 5,876,345 | A | 3/1999 | Eaton et al. |
| 5,902,308 | A | 5/1999 | Murphy |
| 5,906,579 | A | 5/1999 | Vander Salm et al. |
| 5,908,445 | A | 6/1999 | Whayne et al. |
| 5,919,129 | A | 7/1999 | Vandre |
| 5,935,075 | A | 8/1999 | Casscells et al. |
| 5,938,595 | A | 8/1999 | Glass et al. |
| 5,951,471 | A | 9/1999 | de la Rama et al. |
| 5,951,482 | A | 9/1999 | Winston et al. |
| 5,957,903 | A | 9/1999 | Mirzaee et al. |
| 5,980,471 | A | 11/1999 | Jafari |
| 5,984,909 | A | 11/1999 | Lurie et al. |
| 6,001,085 | A | 12/1999 | Lurie et al. |
| 6,023,638 | A | 2/2000 | Swanson |
| 6,141,576 | A | 10/2000 | Littmann et al. |
| 6,178,346 | B1 | 1/2001 | Amundson et al. |
| 6,238,339 | B1 | 5/2001 | Fiddian-Greene et al. |
| 6,258,083 | B1 | 7/2001 | Daniel et al. |
| 6,400,980 | B1 | 6/2002 | Lemelson |
| 6,445,939 | B1 | 9/2002 | Swanson et al. |
| 6,458,088 | B1 | 10/2002 | Hurtak et al. |
| 6,498,941 | B1 | 12/2002 | Jackson |
| 7,329,223 | B1 * | 2/2008 | Ainsworth et al. ........... 600/300 |
| 2002/0038120 | A1 | 3/2002 | Duhaylongod et al. |

OTHER PUBLICATIONS

Casscells W, Hathorn B, David M, Krabach T, Vaugh W, McAllister H, et al., "Thermal detection of Cellular Infiltrates in Living Atherosclerotic Plaques: Possible Implications for Plaque Rupture and Thrombosis." *Lancet* 1996, vol. 347, 1447-1451.

Eina V S. "Laser Doppler Fiberscope Anemometer for In Vivo Blood Flow Measurements." *Optical fibers in Medicine VIII* 1993, 62-73.

Hangiandreou N, Toggart E, Mistretta C. "Investigation of the Performance of Two Types of the Doppler Catheter in Vitro." *Catheterization and Cardiovascular Diagnosis* 1989, vol. 18, 108-117.

Ikeda U, Takahashi M, Shimada K. "Monocyte-Endothelial Cell Interaction in Atherogenesis and Thrombois." *Clinical Cardiology* 1997, vol. 21, 11-14.

Kern M, de Bruyne B, Pijls N. "From Research to Clinical Practice: Current Role of Intracoronary Physiologically Based Decision making in the Cardiac Catherization Laboratory." *Journal of the American College of Cardiology* 1997, vol. 30, 613-620.

Kilpatrick D, Kajiya F, Ogasawara Y. "Fiber Optic Laser Doppler Measurement of Intravascular Velocity." *Australasian Physical and Engineering Sciences in Medicine* 1998, vol. 11, 5-14.

Nishhara H, Koyama J, Hoki N, Kajiya F, Hironaga M, Kano M. "Optical-Fiber Laser Doppler Velocimeter for High-Resolution Measurement of Pulsatile Blood Flows." *Applied Optics 1982*, vol. 21,1785-1790.

Serruys P, di Mario C, Piek J, Shcroeder E, Vrints C, Probst P, de Bruyne B, et al., "Prognostic Value of Intracoronary Flow Velocity and Diameter Stenosis in Assessing the Short- and Long-Term Outcomes of Coronary Balloon Angioplasty: *The DEBATE Study*." Circulation 1997, vol. 96, p. 3369-3377.

Stefandadis C, Diamantopoulos L, Vlachopoulos C, Tsiamis E, Dernellis J, Toutouzas K, et al. "Thermal Heterogeneity Within Human Atherosclerotic Coronary Arteries Detected In Vivo: A New Method of Detection by Application of a Special Thermography Catheter." *Circulation* 1999, vol. 99, 1965-71.

Moslem A, "Transmission properties of optical fibers at two laser wavelengths: 660 nm & 2100 nm", PTICAL Materials, Aug. 9, 1991, Center for Laser Research, Oklahoma State University, p. 27-41.

Doucette J., Corl D., Payne H., Flynn A., Goto M., Nassi M., Segal J. "Validation of a Doppler Guidewire for Intravascular Measurement of Coronary Artery Flow Velocity", Circulation 1992, vol. 85, 382-385.

Dib N., Bajwa T., Shalev Y., Nesto R., Schmidt D., "Validation of Doppler FloWire for Measurement of Coronary Flow Reserve in Humans". *Catheterization and Cardiovascular Diagnosis* 1998, vol. 45, 382-385.

Pijls N., Van Gelder B., Van der Voort P., Peels K., Bracke F., Bonnier H., El Gamal M., "Fractional Flow Reserve: A Useful Index to Evaluate the Influence of an Epicardial Coronary Stenosis on Myocardial Blood Flow." *Circulation* 1995, vol. 92, 3183-3193.

Davis R., "Bursting the Deadly Danger of Aortic Aneurysms", USA Today, Mar. 16, 2000, Section 10D.

Krohn D., "Two Ways of Sensing with Fibers for Two Kinds of Applications", 1998 *The Photonics Design and Applications Handbook*, Sensors, H-203.

Engineering & Marketing Staff, "An Introduction to Fiber Optics", 1998 *The Photonics Design and Applications Handbook*, Fiber Optics, H-176.

Bhatia V., Murphy K., de Vires M., Sen M., D'Alberto T.,"A Comparative Evaluation of the Types and Applications of Various Sensors" 1998, *The Photonics Design and Applications Handbook*, Sensors, H-199.

McCann B., "Three Silica-Core Fibers Rise to Top in Medical Laser Uses", 1998, *The Photonics Design and Applications Handbook*, Fibers/Medical Lasers, H-209.

McCann B., "Fiber Holds the Key to Medical Lasers' Success", May 1990, *Photonics Spectra*, p. 127.

Bridget Hurley's Lab Book 5449, pp. 28-29, Mar. 1, 2000.

Jeff Ellis, Lab Book 5528, pp. 103-107, Feb. 15, 2000.

* cited by examiner

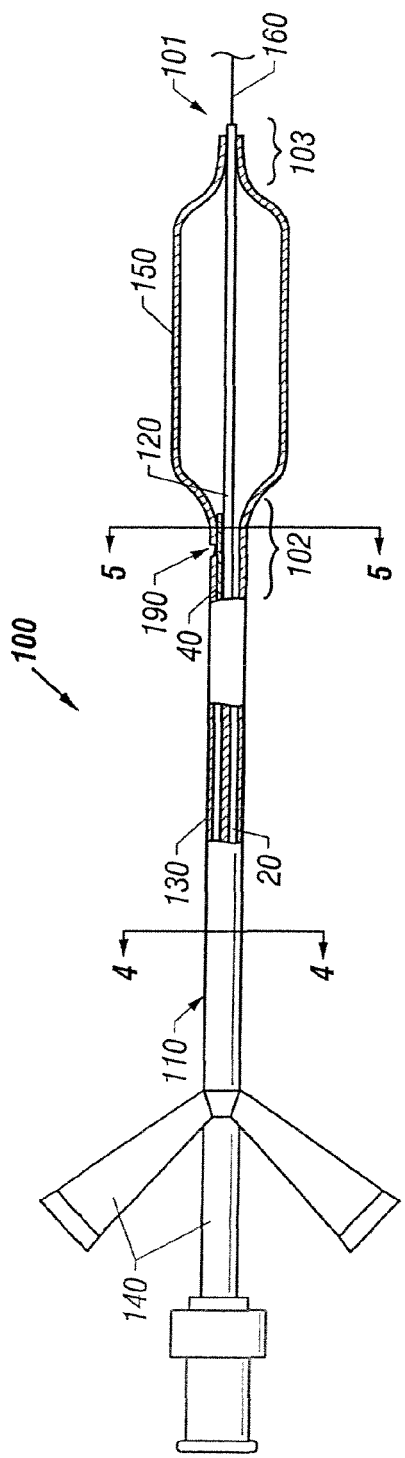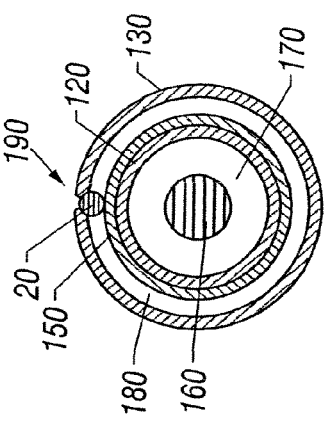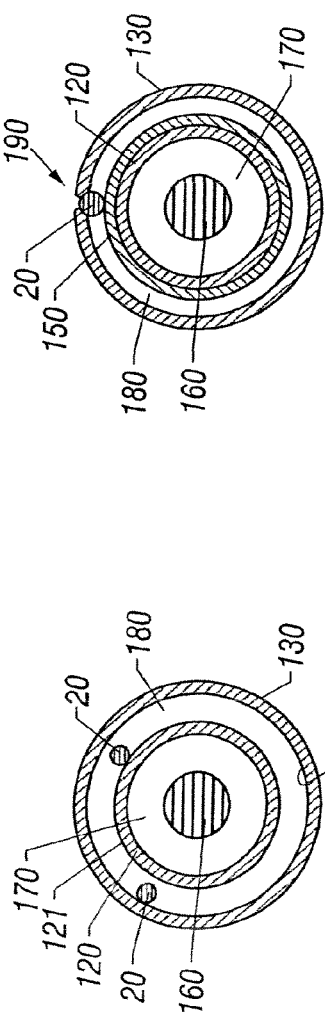

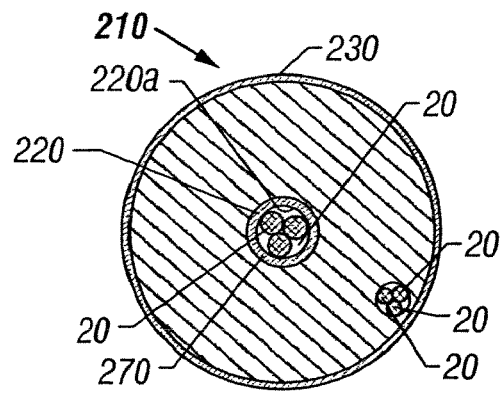
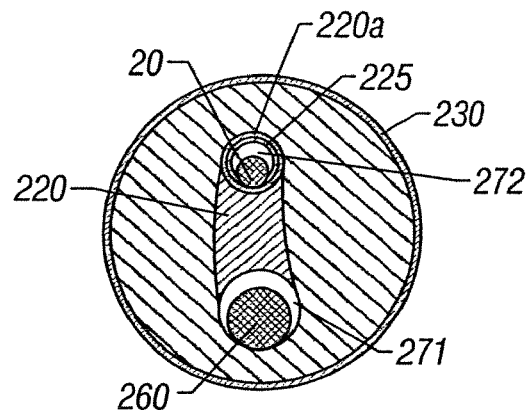
FIG. 7   FIG. 8
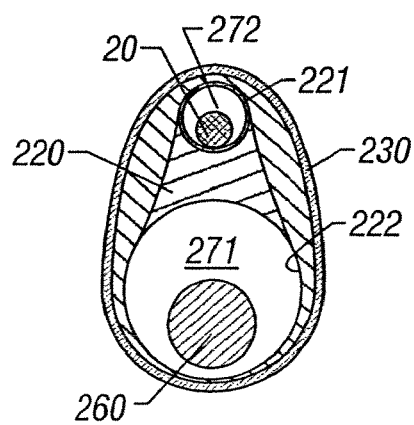
FIG. 9

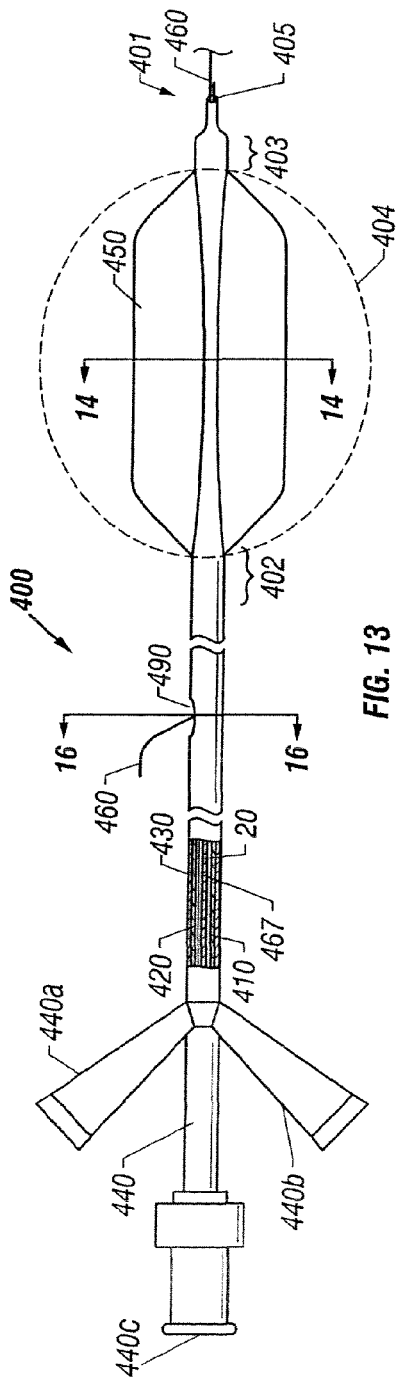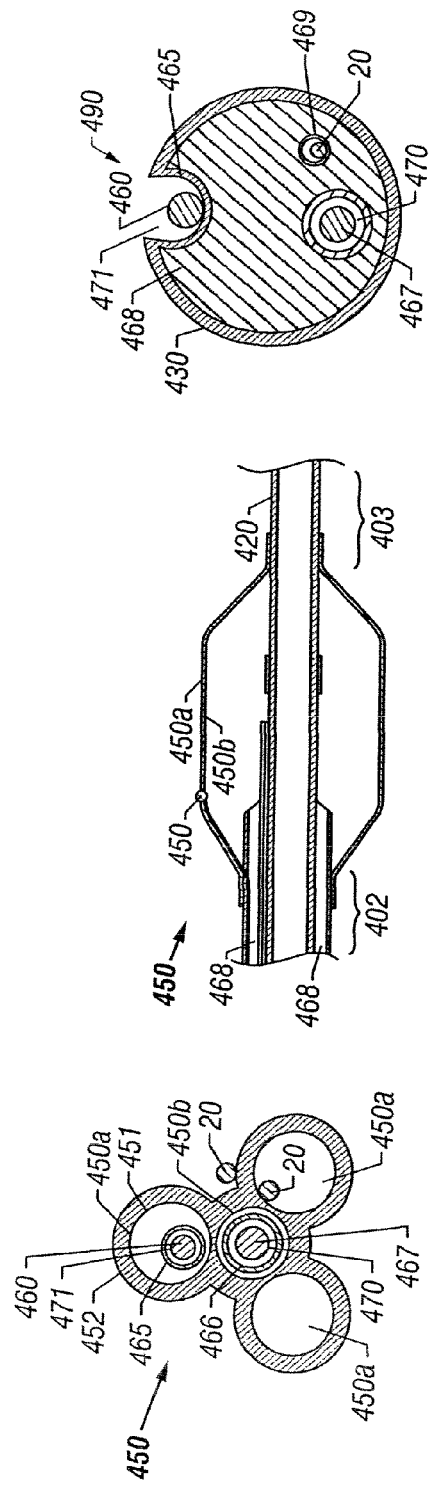

CATHETER WITH OPTICAL FIBER SENSOR

CROSS-REFERENCE TO RELATED APPLICATIONS

This is a continuation of prior U.S. patent application Ser. No. 09/872,310, filed on May 31, 2001, now issued as U.S. Pat. No. 7,329,223 on Feb. 12, 2008.

FIELD OF THE INVENTION

This invention relates to the field of medical diagnosis and treatment by means of an intravascular device. More specifically, the present invention relates to a treatment catheter incorporating an optical fiber capable of providing diagnostic information before, during, and after the procedure.

DESCRIPTION OF RELATED ART

Arteriosclerosis, or more specifically atherosclerosis, is a common human ailment arising from the deposition of fatty-like substances, referred to as atheroma or plaque, on the walls of peripheral and coronary blood vessels. When deposits accumulate in localized regions of a vessel, blood flow can be occluded or restricted, increasing the risk of heart attack or stroke.

Numerous approaches for reducing and removing such vascular deposits have been proposed, including balloon angioplasty, where a balloon-tipped catheter is used to dilate a region of atheroma; atherectomy, where a blade or other cutting element is used to sever and remove the atheroma; and laser angioplasty, where laser energy is used to ablate (i.e., remove) at least a portion of the atheroma. The vast majority of these therapeutic devices, however, are being used with very little information about the in vivo biological environment, including for example, the hemorheology, vascular biology or histology and histochemistry of the vasculature being treated. Without such information available to the physician, "lesion specific" treatment, as well as preventive measures, cannot be adequately envisioned or planned.

To aid the vascular therapeutic approaches above, a number of techniques for transluminal imaging of the atheroma and other diseased regions of a blood vessel have been proposed, including endoscopic and ultrasonic imaging techniques. Some of these techniques involve the use of an intravascular catheter device that is positioned at a desired location within the blood vessel to be treated or imaged. Many of these diagnostic devices have limitations that require measurement of properties, e.g. pressure or flow rate, at locations far removed from the specific site of disease such that accurate diagnosis is already compromised by merely using the device. In addition, most of the diagnostics are not part of the therapeutic phase; therefore, the diagnostic device must be removed in order to treat the patient with a treatment device, for example, a balloon catheter or stent. The result is that therapeutic strategies are often unilaterally rendered without relevant information concerning the lesion, surrounding vasculature, or the biomechanical environment—information which, if available, could be appropriately used to improve both acute and chronic outcomes for the patient.

In the medical field, optical fibers have generally been used to illuminate and view various interior parts of the human body. Example devices include fiber optic scopes. In some medical applications, fiber optic devices have been employed with catheters to either diagnose or treat conditions within patients.

SUMMARY OF THE INVENTION

The present invention directs to an apparatus that performs therapeutic treatment and diagnosis of a patient's vasculature through the use of an intravascular device having an optical fiber disposed therein. In an embodiment, the apparatus includes an intravascular device to perform a therapeutic treatment and at least one optical fiber disposed through the intravascular device. The optical fiber is configured to provide diagnostic information before, during, and after the therapeutic treatment. In an embodiment, diagnostic information includes vessel and blood characteristics such as hemodynamic characteristics, hematological parameters related to blood and blood components, and thermal parameters of the vasculature.

BRIEF DESCRIPTION OF THE DRAWINGS

The present invention is illustrated by way of example and not limitation in the accompanying figures:

FIG. 3 is a side view showing a partial cross-section of another embodiment of a catheter-based intravascular device having an optical fiber within an intraluminal space of the catheter shaft outer member.

FIG. 4 is a cross-sectional view of the catheter-based system of FIG. 3 with the optical fiber secured to the outer surface of the catheter shaft inner member.

FIG. 5 is a cross-sectional view of the catheter-based system of FIG. 3 showing the window or notch on the catheter shaft outer member.

FIG. 7 is a cross-sectional view of the catheter-based system of FIG. 6 with the optical fiber within a single lumen catheter shaft.

FIG. 8 is a cross-sectional view of the catheter-based system of FIG. 6 with the optical fiber within one lumen of a two-lumen catheter shaft.

FIG. 9 is a cross-sectional view of the catheter-based system of FIG. 6 with the optical fiber within a lumen of one inner member of a two-inner member catheter shaft.

FIG. 13 is a side view showing a partial cross section of another embodiment of a catheter-based intravascular device having an optical fiber within a balloon of a catheter.

FIG. 14 is a cross-sectional view of the catheter-based system of FIG. 13 with the optical fiber secured onto the inner surface or outer surface of a multi-lobe balloon.

FIG. 15 is a cross-sectional side view of the catheter-based system of FIG. 13 with the optical fiber secured between two balloon layers of a single lobe balloon.

FIG. 16 is a cross-sectional view of the catheter-based system of FIG. 13 showing the guidewire exit notch on the catheter shaft outer member.

DETAILED DESCRIPTION OF THE INVENTION

Embodiments of apparatuses and methods to perform therapeutic treatment and diagnosis of a patient's vasculature through the use of an intravascular device having at least one optical fiber disposed therethrough are described.

In the following detailed description, numerous specific details are set forth in order to provide a more thorough understanding of the present invention. However, it will be apparent to those skilled in the art to which this invention pertains that the present invention is not limited in scope by these specific details. In other instances, well-known devices, methods, procedures, and individual components have not been described in detail so as not to obscure aspects of the present invention.

Figure 1A:
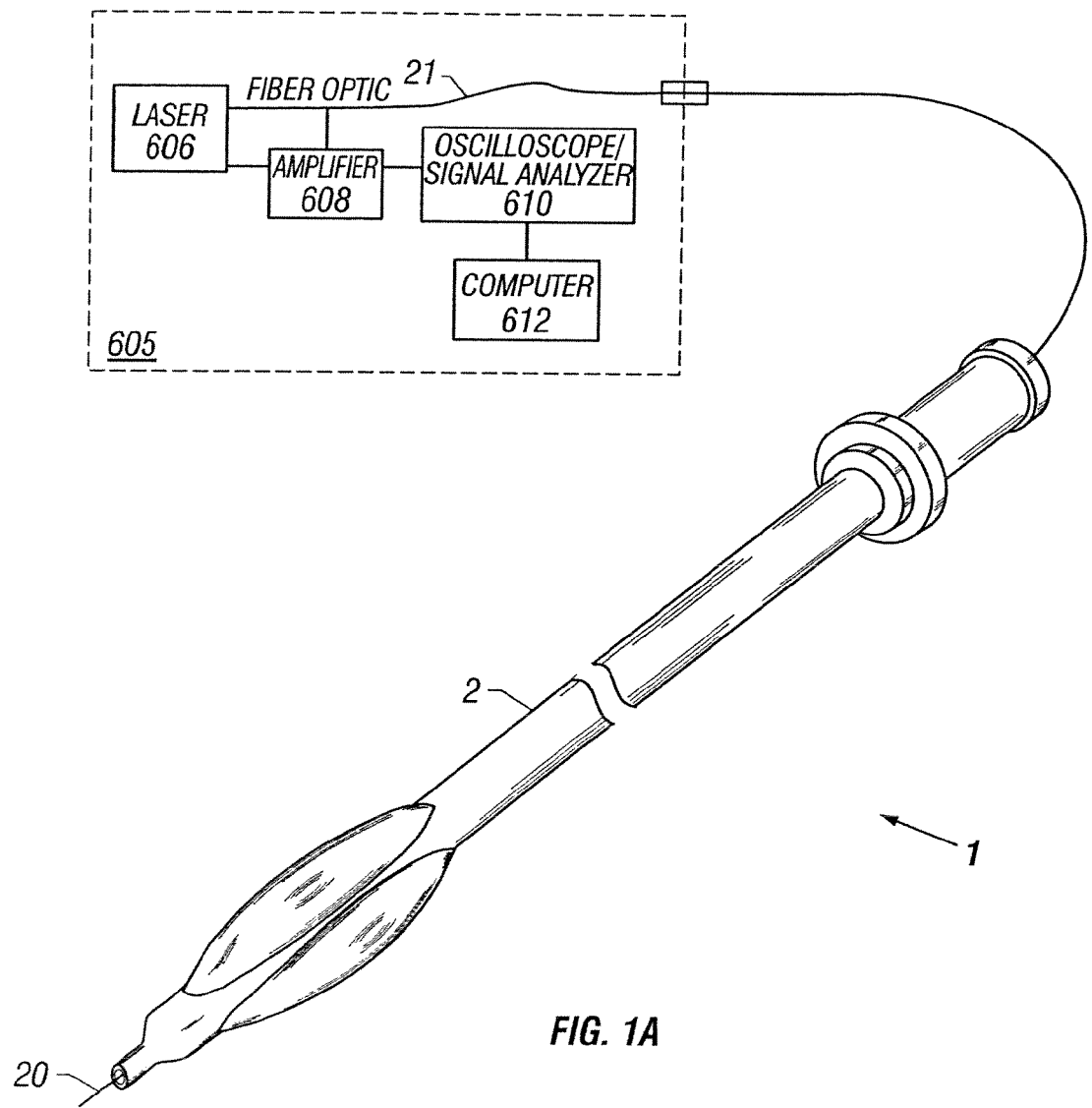
FIG. 1A is a perspective view showing an embodiment of an intravascular device, such as a balloon catheter, having an optical fiber coupled to a data processing system.
Figure 1B:
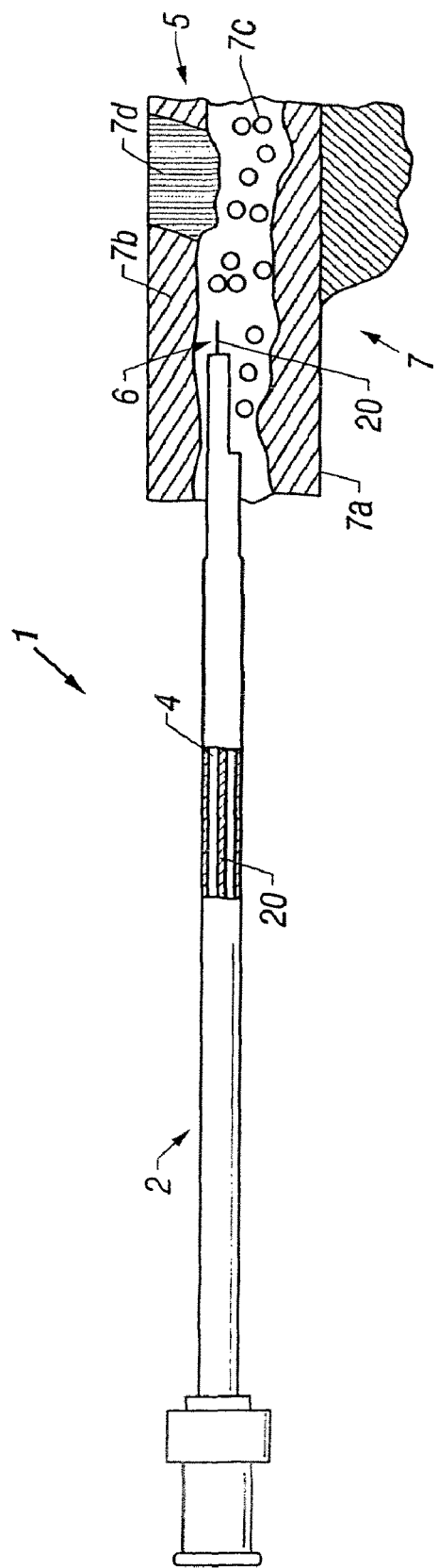
FIG. 1B is a side view showing embodiment of balloon catheter of FIG. 1A positioned within a vasculature of a patient (for clarity, balloon is not shown).

FIGS. 1A-1B illustrate generally an exemplary apparatus 1 of the present invention coupled to a data processing system 605. FIG. 1A illustrates a perspective view of exemplary apparatus 1, while FIG. 1B schematically illustrates apparatus 1 positioned within the vasculature 5 of a patient. Apparatus 1 generally includes an intravascular device 2 to perform a therapeutic treatment, such as angioplasty, stenting, radiation, drug delivery, etc, and at least one optical fiber 20 disposed within the intravascular device 2 configure to provide diagnostic information before, during, and after the therapeutic treatment. The intravascular device 2 may include any medical device, such as a catheter or a guidewire, which is used in treatment of intravascular conditions. The optical fiber 20 may be fixedly coupled to the intravascular device 2 at least one point 4 (shown in FIG. 1B) on the intravascular device 2. Alternatively, optical fiber 20 may be movable, e.g. slideable, within intravascular device 2.

Typically, the optical fiber 20 filament is made of at least two concentrically arranged elements: a central core and a cladding surrounding the core. The "functional" part of the optical fiber is the core—the part that actually transmits the light. The core is made of drawn or extruded silica (glass) or plastic, although other materials may be used. The cladding is usually made of the same material as the core, but with slightly lower index of refraction. This index difference causes total internal reflection to occur within the optical fiber so that the light is transmitted down the fiber and does not escape through the side walls of the optical fiber.

In one embodiment, the optical fiber(s) 20 described above has an outer diameter in the range of approximately 30 to 250 microns; however, other optical fiber diameters are within the scope of this invention. It should be noted that the diameter of the optical fiber core generally has a much lower diameter, for example in the range of about 5-25 microns.

Continuing with reference to FIGS. 1A-1B, in an embodiment, optical fiber(s) 20 may include a single-filament optical fiber. In another embodiment, optical fiber 20 may include two bundles of fibers or alternatively a pair of single fibers. In a single-filament optical fiber construction, light from a laser source 606 in data processing system 605 is transmitted via optical fiber strand 20 and a connecting optical fiber 21 to a reflecting target 7. Optical fiber 20 then receives and transmits the reflected light to a detector/signal analyzer 610 and the light signal is further analyzed in a computer system 612. An amplifier 608 may be used to enhance the light signal. In a multiple optical fiber filament or optical fiber bundle configuration, one optical fiber filament or bundle transmits light to a reflecting target 7; the other receives and transmits the reflected light to a detector. The intensity of the detected light depends on how far the reflecting target 7 is from the optical fiber 20. The reflecting target 7 may include a body vessel 7a (or a body organ), as well as any object associated with or within the vessel 7a (or the body organ), for example a vessel wall 7b, blood particles 7c (or any other fluid within the vessel), a stenosed vessel area 7d (or a treatment area), or any component of the arterial wall.

During a medical procedure, a portion of the optical fiber(s) 20, for example a distal tip 6 of the optical fiber 20 (shown schematically in FIG. 1B) is exposed to or has unobstructed contact with the vasculature 5 of a patient at least at one location along the intravascular device 2. The optical fiber(s) 20 typically provides the intravascular device 2 with the capability to sense vessel and blood characteristics, including but not limited to hemodynamic characteristics, hematological parameters related to blood and blood components, and thermal parameters of the vasculature, lesion, or body site being treated.

Possible target hemodynamic characteristics or variables include blood flow velocity and velocity profile characteristics. The detection of stagnant or recirculating flow regions may relate to propensity of cell adhesion to the endothelium, whereas the detection of slightly turbulent flow may indicate a stenosis that could be angiographically silent. In addition, the levels of shear force may be important for detecting disease-prone regions or shear-induced platelet activation. There are other hemodynamic variables, such as local pressure gradient, that could also be measured or derived from measurements by the optical fiber of the present invention with the intent of identifying regions at high risk for clinical complication.

As stated above, optical fiber 20 disposed within the intravascular device 2 is configured to sense and thus may be used to measure or allow measurement of temperature, pressure, flow, velocity, turbulence, shear stress, etc., of a treatment site. A physician may then use this information in making treatment decisions. For example, if the optical fiber 20 identifies flow discontinuities or abnormal flow rates and the intravascular device 2 is a balloon catheter, the physician could use this information to optimize an angioplasty. Or, if the optical fiber 20 is disposed within an intravascular device 2 such as a stent delivery system, the physician can use the information to optimize the dilatation of the stent.

Furthermore, the optical fiber described above may be incorporated in intravascular devices to address numerous clinical challenges. Such clinical challenges may include, but are not limited to, the prevention and/or treatment of restenosis, chronic total occlusion, saphenous vein graft (SVG) disease, acute myocardial infarction, restenotic lesions, small vessels, dissections, long lesions and diffuse disease, acute or threatened closure, bifurcation lesions, ostial lesions, left main coronary artery (LMCA) disease, aneurysms, vulnerable plaques, etc.

Figure 2:
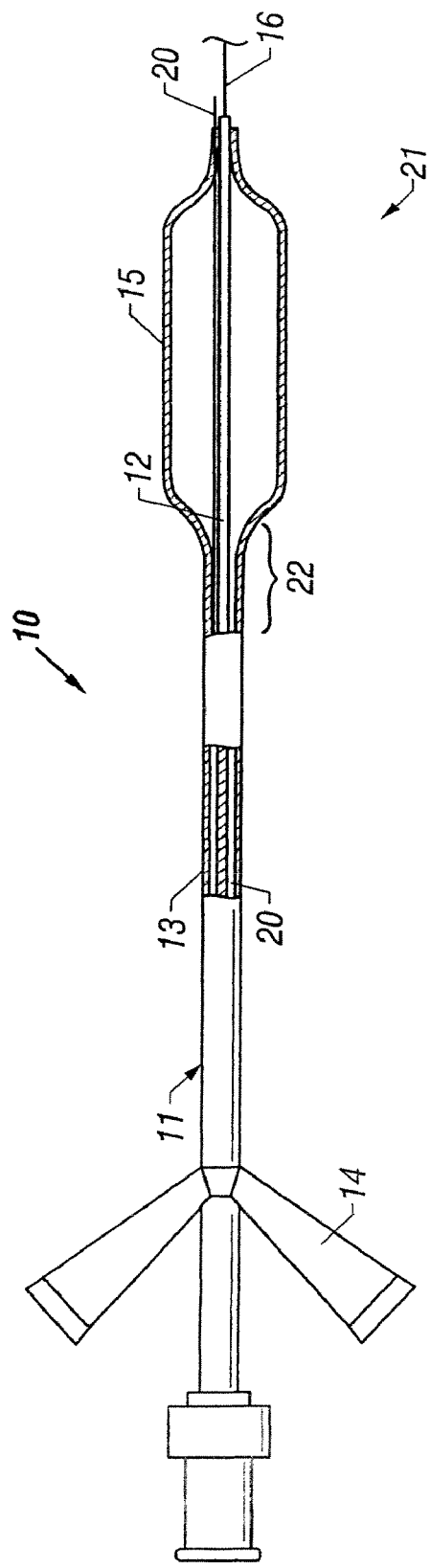
FIG. 2 is a side view showing a partial cross section of an embodiment of a balloon catheter having an optical fiber.

FIG. 2 schematically illustrates a intravascular device 10 embodying features of this invention, such as an over-the wire (OTW) balloon catheter 10 to perform therapeutic treatment and at least one optical fiber 20 disposed within the OTW balloon catheter 10 to obtain diagnostic information before, during, and after the therapeutic treatment. The optical fiber(s) 20 may be fixedly coupled to the balloon catheter 10 at least one point on the balloon catheter 10. Alternatively, the optical fiber 20 may be movable, e.g. slideable, within balloon catheter 10.

The configuration, size, materials, etc. of optical fiber(s) 20 disposed within balloon catheter 10 have been described above. The optical fiber(s) 20 of balloon catheter 10 is configured to sense vessel and blood characteristics, including but not limited to hemodynamic characteristics, hematological parameters related to blood and blood components, and thermal parameters of the vasculature, lesion, or body site being treated.

In one embodiment, balloon catheter 10 includes an elongated catheter shaft 11 having a tubular inner member 12 and an elongated member 13 disposed about the tubular inner member 12. An expandable member, for example an inflatable balloon 15, is disposed at and coupled to a distal end of the elongated catheter shaft 11. In one configuration, the inflatable balloon 15 is coupled to the distal end of the tubular inner member 12. An adapter such as a proximal triple port sidearm 14 is secured to the proximal ends of the inner and outer members 12, 13. Triple port sidearm 14 allows a port for guidewire 16 insertion, another port for passage of an inflating medium (not shown) for balloon 15 inflation, and a third port for insertion of the optical fiber 20.

Continuing with reference to FIG. 2, generally the catheter shaft tubular inner member 12 extends from the proximal sidearm 14 to a catheter distal tip 21 while the elongated member 13 extends from the proximal sidearm 14 to a balloon proximal seal area 22, where the elongated member 13 is placed over and is fused to the proximal end of the balloon 15. Catheter shaft tubular inner member 12 may include at least one lumen longitudinally disposed therethrough that may be used by a guidewire 16 to position the catheter's distal tip, including the balloon 15, over the area within the body lumen that is to be treated.

Balloon 15 may have a single lumen/single lobe arrangement, a multi-lumen/multi-lobe configuration or a combination thereof and may include tapered proximal and distal ends for enhanced treatment delivery, improved body lumen access, better balloon refolding, etc. The configuration of the inflatable balloon 15 generally depends on the type of application in which the balloon catheter 10 is to be used as well as other factors such as manufacturing preferences. For example, when used in the dilatation of a vessel, inflatable balloon 15 may generally have a single lumen design. When used for radiation therapy or drug delivery applications, catheter 10 may typically include a balloon 15 having a multi-lumen configuration for better centering within a body lumen.

The catheter shaft elongated member 13 may be formed of suitable polymeric material such as high density polyethylene, a polyester such as Hytrel® (product of DuPont), polyether-ether-ketone (PEEK) or a variety other polymeric materials. The balloon 15 may be manufactured using balloon materials, such as Pebax™, nylon, polyethylene, polyurethane, or polyester. Materials for use in fabricating the balloon 15 of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.). The catheter shaft tubular inner member 12 may be formed of the same material as the elongated member 13 or a lubricious material such as a fluoropolymer or a hydrophilic material, e.g. the ethylene ethyl acrylate copolymer. The low friction surface of the inner wall of tubular inner member 12 facilitates the advancement of a guidewire 16 within the tubular inner member 12 lumen. The tubular inner member 12 may be a co-extruded member so that the exterior is compatible for fusion bonding to the balloon 15 and the interior has a lubricious surface.

Catheter 10 incorporating optical fiber(s) 20 of the present invention may be used to provide quantitative assessments of a cardiovascular treatment site. For example, the optical fiber(s) 20 of catheter 10 may be used prior to the treatment of a stenosed vasculature to (a) provide information to the physician (e.g., cardiologist) regarding the severity of the stenosis or disease in the vessel area of interest, (b) to indicate to the cardiologist when a treatment procedure is done, or (c) to allow the cardiologist to determine if the treatment is causing any additional damage. As another example, the optical fiber(s) 20 of catheter 10 may be used following treatment, either immediately or any reasonable time later, to assess the effectiveness and/or success of the treatment.

It will be noted that catheter 10 may include any catheter type known in the art, for example an angioplasty catheter, a radiation delivery catheter, a stent delivery catheter, a drug delivery catheter, an imaging catheter, as well as any other type of medical catheters used in the field. Catheter 10 may be a single lumen or multi-lumen catheter design and may have an "over-the-wire" (OTW), "standard Rapid Exchange" (standard RX), "tip-RX", or any other catheter configuration known in the art.

When disposed within the balloon catheter 10, the optical fiber(s) 20 may be positioned in a number of configurations, for example within a lumen of the shaft inner member, within an intraluminal gap or lumen between the catheter shaft inner and outer members, coupled to the balloon or within the balloon lumen(s), or within a catheter sheath enveloping the catheter shaft. These fiber optic/catheter configurations are discussed in detail below.

Fiber Optic Sensor Through Catheter Shaft Outer Member

FIGS. 3-5 illustrate an exemplary catheter-based system 100 having at least one optical fiber 20 through a catheter shaft 110 having an elongated member 130 disposed about a tubular inner member 120. An adapter such as a proximal sidearm 140 may be secured to the proximal ends of the inner and outer members 120, 130. Depending on the type of application in which it is to be used, the catheter-based system 100 may include an expandable member, for example a balloon 150, which is disposed at and coupled to a distal end of the catheter shaft 110.

In one embodiment, at least one optical fiber 20 is inserted into the intraluminal space or gap 180 between the outer member 130 and the inner member 120. In one configuration, the optical fiber 20 may be movable, e.g. slideable, within intraluminal space or gap 180. In another configuration, the optical fiber 20 may be fixedly coupled (i.e., secured) to the inner surface 131 of the shaft outer member 130 at one point 40 along the elongated member 130. For example, if the catheter-based system 100 includes an expandable member, such as a balloon 150, the optical fiber 20 could be jointly bonded at the proximal balloon seal 102. This configuration will allow the optical fiber 20 to bend and "flex" easily as the catheter 100 tracks through tortuous anatomy. For optical transmission, the distal tip of the optical fiber 20 may be exposed through a notch 190 or an optical window present in the outer member 130.

In an alternative embodiment, an optical fiber 20 could be secured to the outer surface 121 of the shaft inner member 120 which may be configured to receive a guidewire 160, within lumen 170, which extends to a distal tip 101 of the catheter 100. In this configuration, the optical fiber 20 could be jointly bonded to the inner member 120 at the distal balloon seal 103. This configuration would allow the optical fiber 20 distal tip to be exposed for optical transmission at the distal tip 101 of catheter 100.

The optical fiber(s) 20 described above may be either a single filament or two or more filaments, bonded or unbonded. In the broad sense of this design, there are many possible embodiments of optical fiber(s). In one embodiment, the optical fiber(s) 20 described above may have an outer diameter in the range of approximately 30 to 250 microns; however, other optical fiber diameters are within the scope of this invention. The optical fiber(s) 20 typically provides catheter 100 with the ability to sense vessel and blood characteristics, including but not limited to hemodynamic characteristics and/or thermal parameters of a blood vessel, lesion, or body site being treated.

Catheter 100 may include any of the catheter configurations and arrangements discussed above. Catheter 100 of the present invention is fabricated of materials similar to those described for catheter embodiment 10 above.

Catheter with Fiber Optic Sensor within Catheter Shaft Inner Member

FIGS. 6-9 illustrate an embodiment of a catheter-based system 200 having at least one optical fiber 20 that is disposed within a lumen 270 of a shaft inner member 220 that is part of the catheter shaft 210. As discussed above, the catheter shaft 210 generally has a shaft inner member 220 coupled to a shaft outer member 230, although other configurations may be practiced within this invention. A multi-port adapter such as a proximal sidearm 240 may be secured to the proximal ends of the inner and outer members 220, 230. Depending on the type of application in which it is to be used, the catheter-based system 200 may include an expandable member, for example a balloon 250, which is disposed at and coupled to a distal end of the catheter shaft 210.

The optical fiber 20 may be either a single fiber optic filament or two or more fiber optic filaments. The optical fiber 20 may be fixedly secured within lumen 270 of the shaft inner member 220 or may be movable within lumen 270 of the shaft inner member 220.

Figure 6:
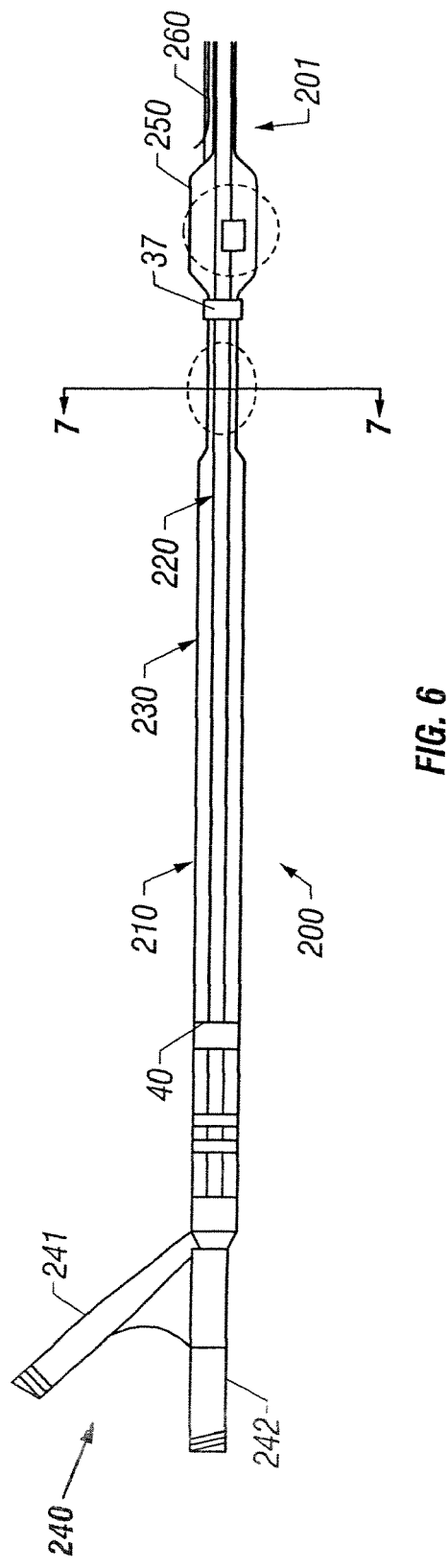
FIG. 6 is a side view showing a partial cross section of another embodiment of a catheter-based intravascular device having an optical fiber within a catheter lumen.

With reference to FIGS. 6 and 7, an embodiment of the present invention is a catheter-based system 200 having a single lumen 270 within the catheter shaft inner member 220. An optical fiber 20 may be fixedly coupled to at least one point 40 on the inner surface 220a of the shaft inner member 220. Alternatively, the optical fiber 20 may be movable within lumen 270 of the shaft inner member 220. It will be noted that the catheter embodiment shown in FIG. 7 cross-section is generally representative of a "tip-RX" type catheter body, where a guidewire 260 (shown in FIG. 6) would be positioned distal to the inflatable balloon 250 and thus would travel only through a distal tip 201 of catheter shaft inner member 220.

With reference to FIGS. 6 and 8, another embodiment of the present invention is a catheter-based system 200 having at least two-lumens 271, 272 within the catheter shaft inner member 220. The catheter shaft inner member 220 extends from a proximal sidearm 240 to the catheter distal tip 201. In this configuration, one lumen 271 would function as a lumen for a guidewire 260 while a second lumen 272 would contain the optical fiber sensor 20. One or more lumens (not shown) may be included as part of the catheter shaft inner member 220 in addition to the guidewire lumen 271 and fiber optic lumen 272. These additional lumens may serve as drug delivery lumen(s), balloon inflation medium lumen(s), radioactive source lumen, imaging agent lumen, and any other therapeutic and/or diagnostic purpose known in the art.

In one embodiment, a tapered mandrel 225 (shown in FIG. 8) may be positioned at a distal end of lumen 272 to provide support to the shaft inner member 220.

The optical fiber 20 disposed within lumen 272 may be fixedly coupled to an interior surface 220a of shaft inner member 220 or be movable, e.g. slideable, within lumen 272. Generally, the lumen 272 containing optical fiber 20 is open at its proximal and distal ends to allow the distal tip of the fiber optic 20 to be exposed to a patient's vasculature during a medical procedure. In another embodiment, lumen 272 receiving the optical fiber 20 may be open at its proximal end, i.e., at sidearm 240, and closed at its distal end. In this configuration, an optical window 37 may be incorporated into the shaft inner member 220, for example at the distal end of inner member 220, to allow the fiber optic 20 to be exposed to the patient's vasculature.

Continuing with reference to FIGS. 6 and 8, using two separate ports 241, 242 at the proximal sidearm 240, one port 241 for the optical fiber 20 and one port 242 for the guidewire 260, allows the optical fiber 20 to be independently advanced and/or rotated within the lumen 272. This would allow a distal tip of the optical fiber 20 to be advanced to the catheter distal tip 201 for optical transmission and then retracted into the lumen 272 during the therapeutic procedure, for example when inflating the balloon to perform an angioplasty. It should be noted, however, that it is within the scope of this invention to have the optical fiber remain exposed within, i.e., in optical contact with, the vasculature of a patient to monitor/investigate treatment progress and/or post treatment outcome.

With reference to FIGS. 6 and 9, in another embodiment, the catheter shaft inner member 220 may have dual-inner member extrusion configuration 221, 222. Catheter shaft inner member 220 may have a first lumen 272 within inner member 221, the lumen 272 being configured to receive an optical fiber 20 therethrough. The catheter shaft inner member 220 may further have a lumen 271 within inner member 222, the lumen 271 being configured to receive a guidewire 260. The first inner member 221 generally runs parallel with the second inner member 222. The first inner member 221 may also be coupled or be adjacent to the second inner member 222 Alternatively, the first and second inner members 221, 222 could extend from the proximal sidearm 240 to the distal catheter tip 201.

In yet another embodiment, the distal end of the first inner member lumen 272, i.e., lumen for the optical fiber 20, would extend through a notch 37 (shown in FIG. 6) in the shaft outer member 230. The optical fiber 20 may be partially or completely fixed within lumen 272 or be movable, e.g. slideable to advance and/or rotate within lumen 272.

The configuration, size, materials, etc. of optical fiber(s) 20 disposed within balloon catheter 200 have been described above. The optical fiber(s) 20 of balloon catheter 200 is configured to sense vessel and blood characteristics, including but not limited to hemodynamic characteristics, hematological parameters related to blood and blood components, and thermal parameters of the vasculature, lesion, or body site being treated.

Balloon catheter 200 may include any of the catheter configurations and arrangements discussed above. Balloon catheter 200 of the present invention is fabricated of materials similar to those described for catheter embodiment 10 above.

Fiber Optic Sensor Through a Sheath

Figure 10:
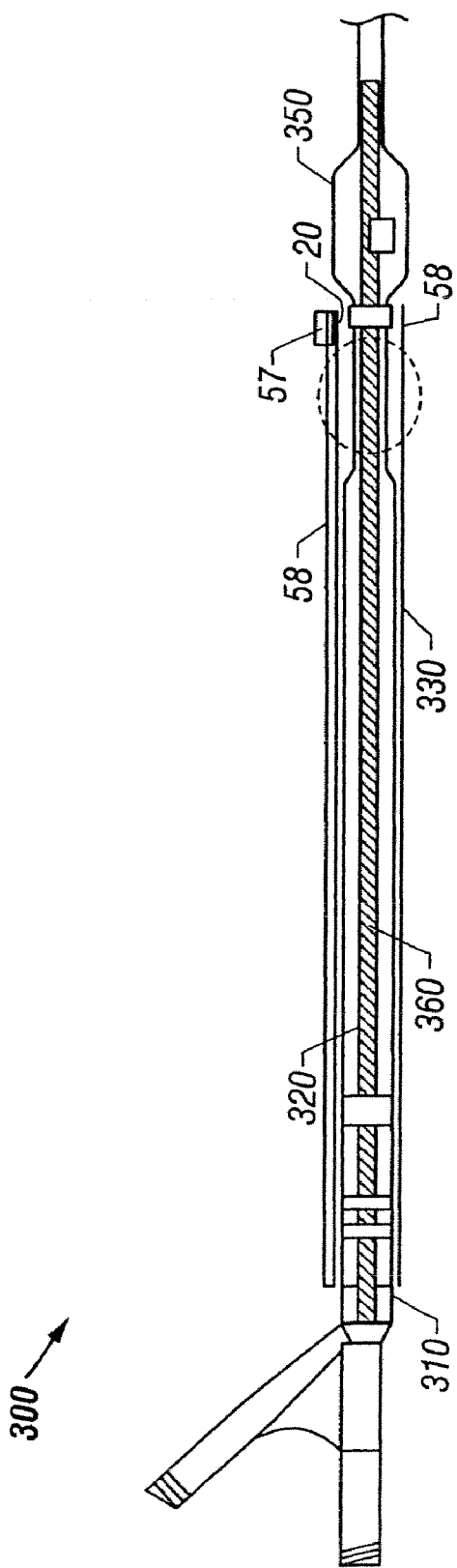
FIG. 10 is a side view showing a partial cross section of another embodiment of a catheter-based intravascular device having an optical fiber through a catheter sheath.
Figure 12:
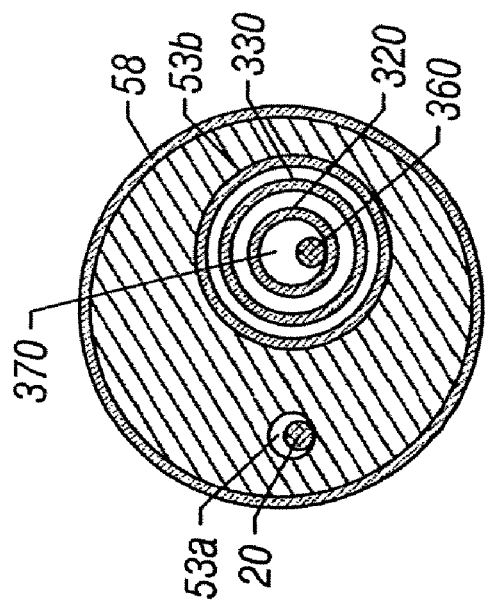
FIG. 12 is a cross-sectional view of the catheter-based system of FIG. 10 with the optical fiber within a lumen of a two-lumen sheath configuration.
Figure 11:
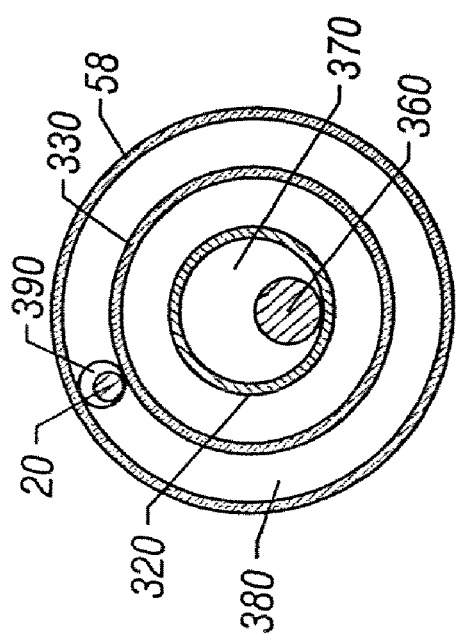
FIG. 11 is a cross-sectional view of the catheter-based system of FIG. 10 with the optical fiber positioned between the catheter sheath and catheter shaft outer member.

FIGS. 10-12 illustrate an example of a catheter-based system 300 that includes a catheter shaft 310 having a catheter shaft outer member 330 coupled to a catheter shaft inner member 320. The catheter shaft inner member 320 has a lumen 370 configured to receive a guidewire 360 for advancing and positioning the catheter 300 at a treatment site. Depending on the type of application in which it is to be used, the catheter-based system 300 may include an expandable member, for example a balloon 350, which is positioned at the distal end of the catheter shaft 310. The catheter-based system 300 further includes a sheath 58 longitudinally slideable over the catheter shaft inner and outer members 320, 330. At least one optical fiber 20 is disposed through, i.e., enveloped within, the slideable sheath 58.

With reference to FIGS. 10 and 11, in one embodiment, at least one optical fiber 20 is disposed within an intraluminal gap 380 longitudinally positioned between the slideable sheath 58 and the catheter shaft inner and outer members 320, 330. In one configuration, the optical fiber 20 may freely move within intraluminal gap 380. In another configuration, the optical fiber 20 may be placed into a thin flexible tubing-like enclosure 390 which may be bonded to at least one point along the outer surface wall of the shaft outer member 330, the inner wall of the sheath 58, and/or the outer surface wall of the shaft inner member 320. This will allow the optical fiber 20 to bend and "flex" easily as the catheter 300, including sheath 58, track through tortuous vessel/organ anatomy. For optical transmission, the tip of the optical fiber 20 may be exposed through a notch or an optical window 57 present in the sheath 58.

The sheath 58 allows the optical fiber 20 to be independently advanced and/or rotated over the therapeutic catheter for optical transmission and then retracted proximal to the balloon 350 and/or a stent (not shown), if a stent is coupled to a catheter, during the therapeutic procedure.

With reference to FIGS. 10 and 12, in a second embodiment, the optical fiber 20 may be inserted into the sheath 58 through a small lumen 53a in a dual lumen extrusion. Lumen 53a may have an interior diameter in the range of approximately 0.005-0.01 in. In one embodiment, lumen 53a has an inner diameter of approximately 0.007 in.

The second lumen 53b of the sheath 58 would allow catheter to be advanced and/or retracted within sheath 58. Lumen 53b may have an interior diameter in the range of approximately 0.050-0.10 in. In one embodiment, lumen 53b has an inner diameter of approximately 0.060 in.

In one embodiment of the configuration presented in FIG. 12, the optical fiber 20 may be partially or completely coupled within the optical fiber lumen 53a. In another embodiment, the optical fiber 20 may be freely movable to advance and/or rotate within the lumen 53a. Similar to the above-described design, sheath 58 may be independently advanced over the catheter for optical transmission and then retracted proximal to the catheter balloon during the therapeutic procedure.

The configuration, size, materials, etc. of optical fiber(s) 20 disposed within balloon catheter 300 have been described above. The optical fiber(s) 20 of balloon catheter 300 is configured to sense vessel and blood characteristics, including but not limited to hemodynamic characteristics, hematological parameters related to blood and blood components, and thermal parameters of the vasculature, lesion, or body site being treated.

Catheter 300 may include any of the catheter configurations and arrangements discussed above. Catheter 300 of the present invention is fabricated of materials similar to those described for catheter embodiment 10 above.

Fiber Optic Sensor Through Catheter Balloon

FIGS. 13-16 schematically illustrate an embodiment of a catheter-based system 400 that includes a catheter shaft 410 having a catheter shaft outer member 430 that is coupled or attached to a catheter shaft inner member 420. The catheter-based system 400 further includes an expandable member, such as a balloon 450, positioned at the distal end of catheter 400. At least one optical fiber sensor 20 may be coupled or attached to the balloon 450. Generally only a distal portion of the optical fiber 20 is coupled to the balloon 450, however, other configurations may be practiced within the scope of this invention. Some portion or all of the remaining length of the optical fiber filament(s) 20 is typically disposed within the catheter shaft 410 and then jointly bonded into a proximal seal 402 formed by the proximal ends of balloon 450 and distal ends of catheter shaft outer members 420, 430. In an embodiment, the length of the optical fiber filament(s) 20 traverses the entire longitudinal length of the catheter shaft 410, exiting the proximal end of the shaft 410 through one of the ports 440a, 440b of adapter 440 which is secured to the proximal ends of the inner and outer members 420, 430.

In one embodiment of this invention, the optical fiber 20 is coupled to the balloon 450 during the balloon blowing process. Typically, as part of the balloon blowing process, a distal section of a balloon tubing is expanded in a balloon mold (not shown) using a combination of heat, pressure, and tensile force. The balloon tubing expansion process continues until a balloon 450 having the desired shape and size is formed in the balloon mold (not shown) from the balloon tubing distal section.

With reference to FIG. 14, in a first embodiment, the optical fiber 20 is molded (and thus affixed or secured) onto the inner surface 451 of the balloon tubing distal section as the tubing expands to form balloon 450. The optical fiber 20 may also be molded (and thus secured) onto the outer surface 452 of the balloon tubing distal section during the balloon blowing process. Alternatively, the optical fiber(s) 20 may be bonded (or secured) to the inner or outer surfaces 451, 452 of balloon 450 following the balloon blowing process. As stated above, some portion or the entire remaining length of optical fiber filament 20 may be positioned within the catheter shaft 410, e.g., inner member 420 and/or outer member 430.

With reference to FIG. 15, in a second arrangement, the optical fiber 20 is positioned between two layers 450a, 450b of balloon tubing. During the balloon blowing process, the optical fiber 20 is molded (and thus affixed) onto at least one of the two layers 450a, 450b of the balloon tubing. Some portion or the entire remaining length of optical fiber 20 may be positioned within the catheter shaft 410, e.g., inner member 420 and/or outer member 430.

In the present invention, laser sealing or bonding techniques such as the square-wave laser design may be desirable. However, bonds may also be done using other balloon bonding techniques known in the art, such as thermal or ultrasonic welds, adhesive bonds (for example glue), or other conventional means.

Balloon 450 may have any configuration known in the art, for example a segmented balloon, a spiral shaped balloon, a fluted balloon, or a combination thereof. In an embodiment, balloon 450 may have a multi-lumen (or multi-lobe) design configuration (as shown in FIGS. 13-16). Alternatively, balloon 450 may have a single lumen design configuration (as shown in FIG. 2). Generally, a balloon catheter having a multi-lobe balloon design may be employed as an intravascular/intraductal centering catheter for use with, but not limited to, a radiation source, an intravascular ultrasound device, a therapeutic drug, etc. A balloon catheter having a single lumen balloon design may be used for, but not limited to, vessel/artery/body lumen dilatation, intravascular stent deployment, intravascular drug delivery, and other medical applications.

The catheter shown in FIGS. 13-16 is a standard "rapid exchange" (RX) design, having a guidewire tubing 465 with a lumen 471 running from the distal tip of the catheter 401 to an exit notch 490 located on the distal portion of shaft 410 approximately 28 cm from the distal tip 401. The most distal end of the catheter generally includes a "soft tip" 405 formed from a single lumen tubing. In one embodiment, the soft tip extrusion 405 is approximately 1 mm long and is attached to the end of guidewire lumen extrusion tubing 465 (shown in FIGS. 14 and 16) that is part of a distal portion of the catheter shaft inner member 420. As noted above, for standard RX catheter design configurations, the guidewire lumen extrusion tubing 465 generally extends from about the distal tip 401 of catheter 400 to an exit notch 490 located on the distal portion of shaft 410.

With reference to FIG. 14, a cross section in the middle of the balloon 450 is schematically illustrated. In this configuration, balloon 450 has three longitudinal lobes 450*a* arrayed around a central lumen 450*b*. The central lumen 450*b* of the balloon is sized to fit a therapy lumen extrusion tubing 466, for example a radiation source lumen tubing 466 that can receive a radiation source 467 through lumen 470 during patient treatment. Generally, at its most distal tip, lumen 470 of the therapy lumen tubing, e.g., radiation source tubing 466 is "plugged" to prevent direct contact between body lumen fluids and the therapy device, e.g., radiation source. In one embodiment, the guidewire lumen extrusion 465 for receiving a guidewire 460 may be longitudinally disposed through one of the balloon lobes 450*a*, however, other guidewire lumen configurations, such as guidewire lumen through the balloon central lumen 450*b* are within the scope of this invention.

Both the guidewire and the therapy lumen extrusions 465, 466 may be manufactured as co-extrusions. In one embodiment, catheter shaft may have an inner member co-extrusion of Primacor and high-density polyethylene (HDPE), with an outer member made of Nylon. Alternatively, catheter shaft may be manufactured as a trilayer extrusion of Pebax or Nylon, Primacor, and HDPE. Typically, the choice of layer materials is directed by the compatibility of the balloon material and the material selected for the catheter. The balloon is formed from Pebax, but could be manufactured from nylon, polyethylene, polyester, or other materials known in the art.

FIG. 15 schematically illustrates a side cross-section through the balloon catheter embodiment 400 showing proximal and distal balloon seals 402, 403. The proximal balloon seal 402 serves to connect the three balloon lobes 450*a* to at least one inflation lumen 468. The radiation source lumen and guidewire lumen extrusions also pass through the proximal balloon seal 402; however, they are not represented in FIG. 15 so as not to obscure the invention. The seal is created by assembling the various tubings and mandrels to support the lumens during processing, placing a shrink tubing (not shown) over the assembly, and applying heat to melt the materials together. The shrink tubing serves to compress the materials in to a compact seal. The preferred method for applying heat is via a laser system, but other options such as inductive heating are possible.

Referring again to FIGS. 13 and 16, in one embodiment, for optimal catheter performance, the outer shaft member 430 along the proximal portion of the catheter shaft 410, i.e., at a catheter shaft location proximal to the guidewire exit notch 490, is formed using a high-stiffness polymer, such as polyether-ether-ketone (PEEK). The inner member 420 is typically formed by the therapy lumen extrusion 466, e.g., radiation source lumen extrusion tubing 466, and may also include the optical fiber 20 (with or without a protective tubing 469). The inflation lumen 468 generally continues through the proximal portion of the shaft 410 and terminates in a multiport side arm or manifold 440 whose design enables the radiation source lumen tubing 466 to connect to a therapy device (not shown), and the inflation lumen 468 to connect to an inflation device (not shown).

The balloon tubing (and thus balloon 450) may be manufactured using any balloon materials, such as resin, Pebax™, nylon, polyethylene, polyurethane, or polyester. Materials for use in fabricating the balloon tubing of the present invention are selected by considering the properties and characteristics (e.g., softness, durability, low stiffness) required by angioplasty balloons, as well as considering properties necessary for successful balloon fabrication (e.g., balloon material compatible with other catheter materials and bonding process, material extruding well, etc.).

The configuration, size, materials, etc. of optical fiber(s) 20 disposed within balloon catheter 400 have been described above. The optical fiber(s) 20 of balloon catheter 400 is configured to sense vessel and blood characteristics, including but not limited to hemodynamic characteristics, hematological parameters related to blood and blood components, and thermal parameters of the vasculature, lesion, or body site being treated.

Catheter 400 may include any of the catheter configurations and arrangements discussed above. Catheter 400 of the present invention is fabricated of materials similar to those described for catheter embodiment 10 above.

Fiber Optic Sensor within a Coil or as Braided Member

Figure 17:
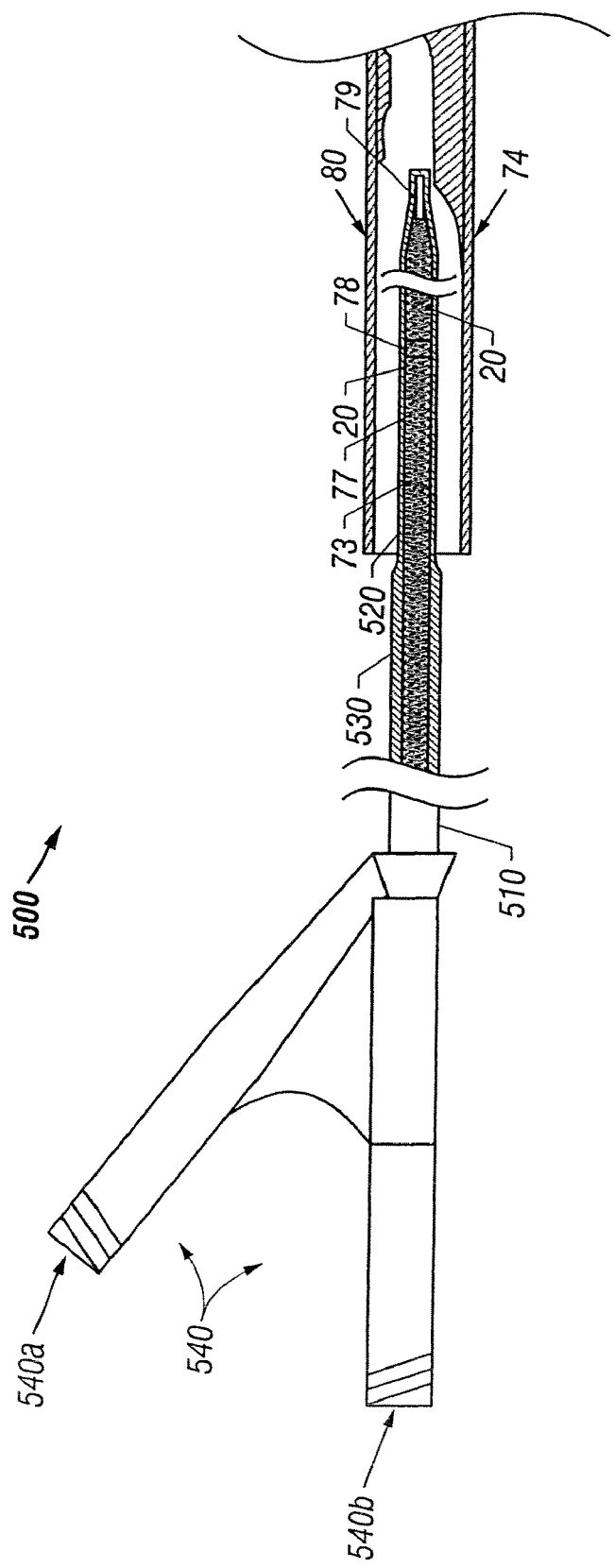
FIG. 17 is a side view showing a partial cross section of another embodiment of a catheter-based intravascular device having at least one optical fiber within a coil-like enclosure.
Figure 19:
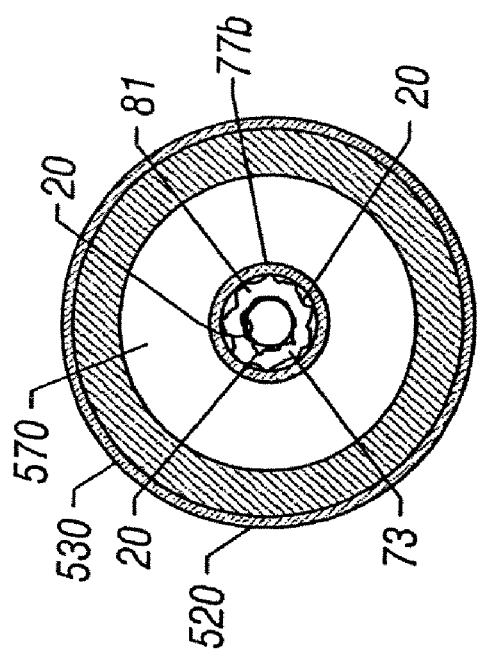
FIG. 19 is a cross-sectional view of the catheter-based system of FIG. 17 with an optical fiber array within a catheter shaft.
Figure 18:
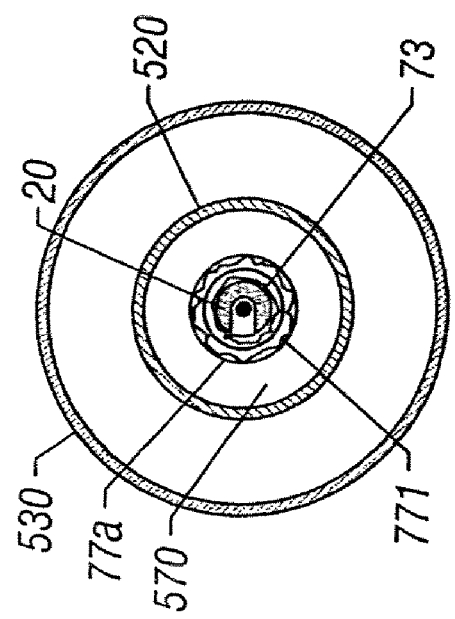
FIG. 18 is a cross-sectional view of the catheter-based system of FIG. 17 with the optical fiber positioned within a coil-like enclosure.

FIGS. 17-19 schematically illustrate a catheter-based system 500 embodying the features of this invention. In an embodiment, catheter 500 includes a catheter shaft 510 having an outer member 530 coupled to a catheter shaft inner member 520, although other configurations may be practiced within this invention. Catheter 500 further includes an elongated member 77 longitudinally disposed within a lumen 570 of catheter shaft inner member 520 and at least one optical fiber 20 which may be disposed either within a lumen 73 the elongated member 77 or arranged over an outer surface 771 of the elongated member 77. In one configuration, the elongated member 77 includes a coil-like enclosure 77*a*. Alternatively, the elongated member 77 may be configured as a braided member 77*b*.

In an embodiment, the length of the optical fiber filament(s) 20 traverses the entire longitudinal length of the catheter shaft 510, exiting the proximal end of the shaft 510 through port 540*a* of adapter 540 which is secured to the proximal ends of the inner and outer members 520, 530. The other port 540*b* of adapter 540 may be used for a number of purposes, including for example to advance a guidewire 560, a radioactive source (not shown), an IVUS device (not shown), or other treatment or diagnostic device through the catheter shaft inner member 520 to a treatment site of a patient's vasculature.

Referring to FIGS. 17-19, in one embodiment, the optical fiber(s) 20 is disposed within a coil-like enclosure 77a using various methods, such as (a) inserting the sensor 20 into the coil 77a, (b) assembling the coil 77a over the optical fiber 20, or any other methods used in the art. In one configuration, the optical fiber 20 is secured (i.e., bonded, affixed) at a point along the inner surface of the coil 77a to allow the optical fiber 20 to bend and flex easily as it tracks through a tortuous anatomy of a vessel 80. Alternatively, the optical fiber 20 may be inserted into the lumen 73 of a braided member 77b, or the braided member 77b could be assembled over the optical fiber 20. The optical fiber 20 may be moveable (e.g. slideable) or secured (i.e., bonded, affixed) at one point along the inner surface of the braided member 77b.

For optical transmission, the optical fiber tip 79 must be exposed through a distal end of the coil 77a or braided member 77b, through a notch 78 in the coil 77a or braided member 77b, or through an optical window 78 on the coil 77a or braided member 77b.

In a catheter-based system such as the system 500 presented in FIGS. 17-19, the optical fiber 20 embodiments presented immediately above could be unattached or slideable within the intraluminal space 570 of catheter shaft inner member 520 or contained within a separate lumen 73 of elongated member embodiments 77a, 77b as discussed above. If incorporated within a separate lumen 73, the optical fiber 20 may be advanced to the distal tip 74 of the catheter 500 for optical transmission during the diagnostic procedure, and then retracted into the lumen 73 during the therapeutic procedure.

With reference to FIGS. 17 and 19, alternatively, in another embodiment, an array of at least two optical fibers 20 may be positioned within a catheter-based system 500. Multiple optical fibers 20 could be bonded to one another in either a braided or parallel fashion. In one configuration, in a catheter-based system 500, the fiber optic array may be unattached or slideable within the intraluminal space of the catheter shaft or contained within a separate lumen 73 as discussed above. In another configuration, multiple optical fiber sensors 20 may be affixed or bonded to the interior wall of a single lumen tubing 81 (shown in FIG. 19) that could be incorporated into a catheter-based system 500.

The configuration, size, materials, etc. of optical fiber(s) 20 disposed within catheter 500 have been described above. The optical fiber(s) 20 of catheter 500 is configured to sense vessel and blood characteristics, including but not limited to hemodynamic characteristics, hematological parameters related to blood and blood components, and thermal parameters of the vasculature, lesion, or body site being treated.

Catheter 500 may include any of the catheter configurations and arrangements discussed above. Catheter 500 of the present invention is fabricated of materials similar to those described for catheter embodiment 10 above.

Method for Performing Treatment and Diagnosis of Vasculature

Figure 20:
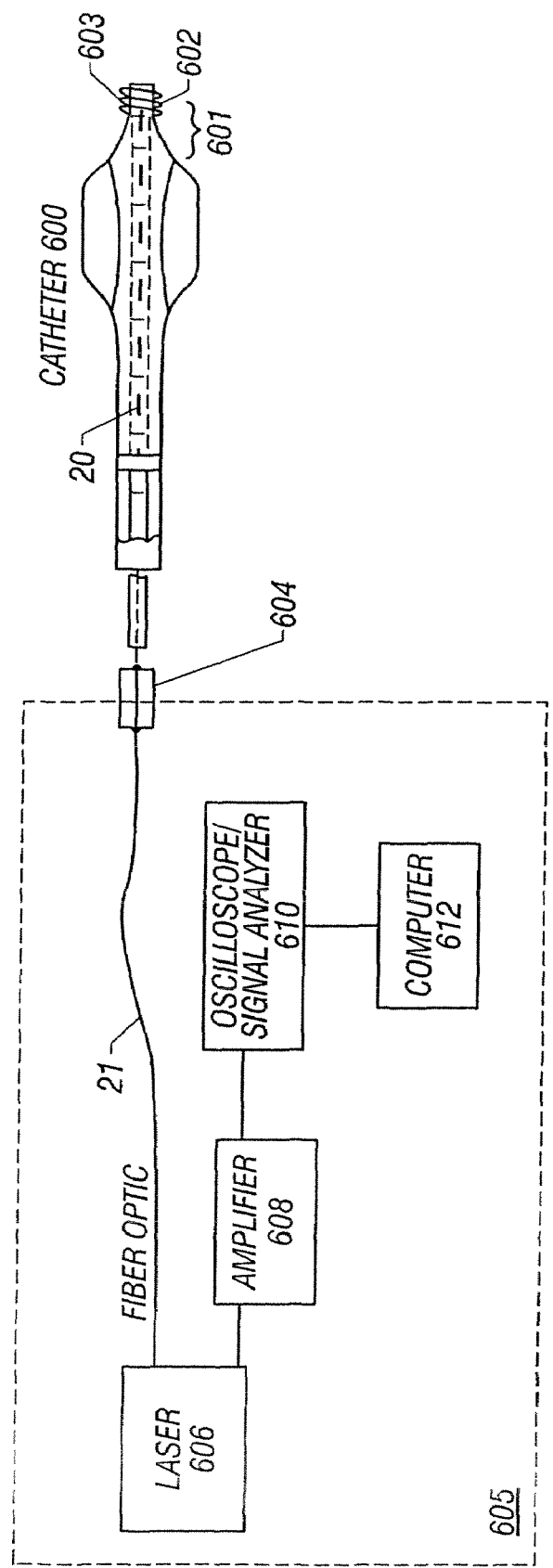
FIG. 20 is a block schematic diagram of an embodiment of an intravascular device, such as a catheter, having an optical fiber coupled to a data processing system.

FIG. 20 illustrates generally one embodiment of at least one optical fiber 20 within a catheter-based system 600 coupled to a data processing system 605. Catheter-based system 600 with at least one optical fiber 20 may include any of the intravascular device and catheter embodiments discussed above and shown in FIGS. 1-19.

With reference to FIG. 20, in an embodiment, the catheter-based system 600 has a catheter body 601 that extends from a hub 604. Catheter 600 includes a balloon 602 disposed at the distal end catheter body 601. A distal portion of catheter body 601 is insertable into a patient according to commonly known methods. If catheter 600 is to be used in a stenting procedure, an expandable metallic structure 603, such as stent 603, may be disposed, i.e., loaded, over the distal most tip of catheter body 601, typically over the balloon 602.

Hub 604 accommodates at least one optical fiber 20 (as shown in FIGS. 1-19). The optical fiber 20 can be connected to a laser source 606 via connecting optical fiber 21. An amplifier 608, a signal processing unit 610, and a computer system 612 may be connected to process the feedback signal received through the fiber optics 20, 21. Laser source 606 can be any continuous-wave signal or a high-repetition-rate pulsed laser. In one embodiment, laser source 606 is a modulated light diode or high-powered laser light source.

The laser source is typically chosen based on the light wavelengths and light source power that facilitate the detection of the particular physical characteristic or variable. Specifically, because the light transmission window of blood is in the red to infrared (IR) range, a light wavelength in the range of 700 nm to 1500 nm may be used. It should be noted that longer wavelengths in the above stated range are desirable as they overcome some of the signal loss due to scattering in the blood. The shorter wavelengths are more energetic and therefore have the potential to cause tissue damage. In one embodiment, a wavelength of approximately 1300 nm may preferably be used.

The light output could be filtered if desired, as a homogenized illumination improves the signal-to-noise ratio. If the red or near-IR spectral range is used, laser diodes could be used as the excitation source to further improve the signal-to-noise ratio. Signal processing unit 610 typically processes a signal from visual or light source data to electronic data or vice versa.

Laser source 606, amplifier 608 and signal processing unit 610 may be connected to a computer system 612, which is typically used for data acquisition, data processing and display and system control. Catheter 600 houses an optical fiber 20 which is coupled to the at least one fiber optic wire 21 to which laser source 606, amplifier 608, signal processing unit 610, and computer system 612 are connected. It is appreciated that any or all of laser source 606, amplifier 608, signal processing unit 610, and computer system 612 can be combined into an independent console unit.

It is appreciated that a variety of components can be used to help generate, transmit and receive fiber optic signals. For example, a mono-chromator can be used to receive light signals transmitted back from the field of interest. The mono-chromator can also be fitted with a photodiode array detector, such as a 512 element intensified silicon photodiode array detector. Furthermore, a high-resolution filter grating can be installed in the mono-chromator in order to sharpen the features displayed in the spectral response for easier peak recognition and spectral analysis. A pulse generator can be used to time the detector response from the output pulse of the laser light signal.

In a typical embodiment of the present invention, a physician, e.g. cardiologist, usually first decides which physical characteristic or variable of a vessel/treatment site is to be investigated (e.g., measured, identified). The physician will generally then insert a intravascular device with an optical fiber into the patient's vasculature and advances it to a specified location in the vasculature. Once the intravascular device is in place, a data processing system is generally operated to transmit (or send) a plurality of light radiation signals via the optical fiber to the specified location in the vasculature. The reflected light radiation signals are transmitted via the optical fiber to a detector in the data processing system. The data processing system then processes these signals to provide information on a display so that the medical professional can view this information and determine how to proceed. The doctor may choose to perform a therapeutic procedure, such as angioplasty or stenting, or decide that further treatment is not required. The doctor may decide that further information on that section of the vasculature is necessary and either continues with the same medical device-based optical fiber or use a different optical fiber to try to obtain different physical characteristic or variable data.

Given their very small outer diameter size (for example, in the range of approximately 30 to 250 microns), the optical fiber(s) of the present invention may also be incorporated within any conventional intravascular device, for example, a catheter, a sheath, a guidewire. When properly coupled to a intravascular device, the optical fiber does not interfere with the functionality and performance of the intravascular device. Furthermore, the design allows the overall dimensions and flexibility of the intravascular device to remain the same.

The intravascular device of the present invention provides several advantages over the relatively few current diagnostic devices used in the art. The diagnostic devices currently available to measure properties such as pressure and/or flow rate are limited in resolution, and are adversely affected by disturbed conditions typically found in the diseased area. In contrast, a intravascular device of the present invention can sense extremely small gradients of parameters throughout the human vascular system and, specifically, in the critical areas surrounding the treatment site to provide more comprehensive information on the disease state. Further, after the diagnosis has been carried out, the devices of the current art must then be replaced with a therapeutic device, whereas the present invention allows for a diagnostic and therapeutic tool in one device.

It should be noted that apparatuses and methods of the present invention are not limited to use in the vascular system only but may be advantageously employed in other body organs and structures, such as the esophagus, the stomach, the colon, the uterus, saphenous vein grafts, heart valves, and other body cavities, lumens, channels, and canals.

Thus, the present invention describes a unique medical device typically used to treat human atherosclerosis that encompasses both diagnostic and therapeutic capabilities. The combined intravascular device and sensor of the present invention allow the invention to sense vessel and blood characteristics, including but not limited to: hemodynamic characteristics, and/or thermal parameters of the diseased vessel or region surrounding the treatment site. The present invention will aid cardiologists in development of lesion specific interventional strategies and preventative medicine for human vascular disease.

We claim:

1. An apparatus comprising:
    an intravascular device to perform a treatment; and
    at least one optical fiber disposed within a coil-like enclosure which concentrically surrounds the at least one optical fiber and disposed within the intravascular device, and the at least one optical fiber is bonded to at least one point along an inner surface of the coil-like enclosure, the at least one optical fiber configured to provide information at least one of before, during, and after the treatment, the information comprising measurements used to optimize the treatment.

2. The apparatus of claim 1 wherein the at least one optical fiber is configured to be inserted within a vasculature and exposed at least at one location along the intravascular device.

3. The apparatus of claim 2 wherein the at least one optical fiber is configured to sense vessel and blood characteristics.

4. The apparatus of claim 3 wherein vessel and blood characteristics are selected from the group consisting of hemodynamic characteristics, hematological parameters related to blood and blood components and thermal parameters of the vasculature.

5. The apparatus of claim 1 wherein the intravascular device is a balloon catheter comprising:
    a catheter shaft having an elongated outer member disposed about a tubular inner member, the tubular inner member having a lumen to receive the at least one optical fiber therethrough; and
    a balloon coupled to a distal portion of the catheter shaft for dilating a stenosed vessel.

6. The apparatus of claim 5 wherein the at least one optical fiber is movable within the lumen.

7. The apparatus of claim 5 wherein the lumen is configured to receive an inflation medium therethrough to inflate the balloon.

8. The apparatus of claim 7 wherein a distal tip of the at least one optical fiber is configured to be inserted within a vasculature and exposed at least at one location along the balloon catheter.

9. The apparatus of claim 8 wherein the at least one optical fiber is configured to sense vessel and blood characteristics selected from the group consisting of hemodynamic characteristics, hematological parameters related to blood and blood components and thermal parameters of the vasculature.

10. The apparatus of claim 5 wherein the tubular inner member has a second lumen extending at least within a distal portion of the tubular inner member, the second lumen being substantially parallel to the lumen having the at least one optical fiber therethrough.

11. The apparatus of claim 10 wherein the second lumen is a lumen selected from the group consisting of guidewire lumen, inflation lumen, radiation source lumen, drug delivery lumen, atherectomy device lumen and laparoscopy lumen.

12. The apparatus of claim 11 wherein a distal tip of the at least one optical fiber is configured to be inserted within a vasculature and exposed at least at one location along the balloon catheter.

13. The apparatus of claim 12 wherein the at least one optical fiber is configured to sense vessel and blood characteristics selected from the group consisting of hemodynamic characteristics, hematological parameters related to blood and blood components and thermal parameters of the vasculature.

14. A system for sensing vessel and blood characteristics, the system comprising:
    a data processing system; and
    an apparatus coupled to the data processing system, the apparatus comprising an intravascular device to perform a treatment and at least one optical fiber disposed within a coil-like enclosure which concentrically surrounds the at least one optical fiber and disposed within the intravascular device, and the at least one optical fiber is bonded to at least one point along an inner surface of the coil-like enclosure, the at least one optical fiber configured to provide information at least one of before, during, and after the treatment, the information comprising measurements used to optimize the treatment.

15. The system of claim 14 wherein a distal tip of the at least one optical fiber is configured to contact a vasculature at least at one location along the intravascular device, the optical fiber configured to sense vessel and blood characteristics selected from the group consisting of hemodynamic characteristics, hematological parameters related to blood and blood components and thermal parameters of the vasculature.

16. A catheter, comprising:
a catheter inner shaft member having a first lumen, an optical fiber within the first lumen, the optical fiber disposed within a coil-like enclosure which concentrically surrounds the optical fiber and the optical fiber is bonded to at least one point along an interior surface of the coil-like enclosure, a second lumen adapted to receive a guidewire, and a third lumen adapted to received a drug, wherein the optical fiber is configured to provide information at least one of before, during, and after a treatment, the information comprising measurements used to optimize the treatment.

17. The catheter of claim 16, wherein a tapered mandrel is disposed near a distal end of the first lumen to provide support to the catheter inner shaft member.

18. The catheter of claim 16, further comprising an inflatable balloon coupled to the catheter inner shaft member, and wherein the third lumen is also adapted to receive an inflation medium.

19. An apparatus comprising:
a trackable intravascular device that can bend to perform a treatment;
a proximal end of the trackable intravascular device, the proximal end configured to send at least one light signal and receive detected light from a distal end of the trackable intravascular device;
the distal end configured to send the at least one light signal being received from the proximal end and also receive detected light from a target;
at least one optical fiber disposed within a coil-like enclosure which concentrically surrounds the at least one optical fiber and disposed within the intravascular device, and the at least one optical fiber is bonded to at least one point along an inner surface of the coil-like enclosure, the at least one optical fiber configured to provide diagnostic information at least one of before, during, and after the treatment; and
an optical window at the distal end that allows optical transmission or reception of light through the optical fiber.

20. A method of sensing vessel and blood characteristics, the method comprising:
inserting an apparatus into a vasculature, the apparatus comprising an intravascular device and at least one optical fiber disposed within a coil-like enclosure which concentrically surrounds the at least one optical fiber and disposed within the intravascular device, and the at least one optical fiber is bonded to at least one point along an inner surface of the coil-like enclosure, the at least one optical fiber to transmit a light radiation signal therethrough;
advancing the apparatus to a location in the vasculature;
operating a data processing system coupled to the apparatus to transmit a plurality of light radiation signals to the location in the vasculature and a plurality of reflected light radiation signals to a detector in the data processing system; and
processing the plurality of reflected light radiation signals to determine vessel and blood characteristics.

21. The method of claim 20, wherein vessel and blood characteristics are selected from the group consisting of hemodynamic characteristics, hematological parameters related to blood and blood components and thermal parameters of the vasculature.

22. A method comprising:
inserting a balloon catheter into a vasculature, the balloon catheter comprising an inflatable balloon disposed at the distal end of a catheter shaft and at least one optical fiber disposed within a coil-like enclosure which concentrically surrounds the at least one optical fiber and disposed within an intravascular device, and the at least one optical fiber is bonded to at least one point along an inner surface of the coil-like enclosure, the at least one optical fiber being coupled with the balloon catheter, the balloon catheter further comprising an expandable metallic structure disposed at a distal end of the catheter shaft and substantially over the inflatable balloon;
advancing the balloon catheter to a location in the vasculature;
operating the balloon catheter and the at least one optical fiber within the vasculature;
operating a data processing system coupled to the balloon catheter to provide vessel and blood characteristics; and
inflating the inflatable balloon to expand the expandable metallic structure within the vasculature.

23. The method of claim 22, wherein operating the data processing system is performed prior, during or after inflating the inflatable balloon.

24. The method of claim 22, wherein the expandable metallic structure is a stent.

25. The method of claim 22, wherein vessel and blood characteristics are selected from the group consisting of hemodynamic characteristics, hematological parameters related to blood and blood components and thermal parameters of the vasculature.

* * * * *